United States Patent
Lee

(10) Patent No.: US 9,782,592 B2
(45) Date of Patent: Oct. 10, 2017

(54) ENERGY EFFICIENT HIGH FREQUENCY NERVE BLOCKING TECHNIQUE

(75) Inventor: Dongchul Lee, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1197 days.

(21) Appl. No.: 13/184,347

(22) Filed: Jul. 15, 2011

(65) Prior Publication Data

US 2012/0016448 A1 Jan. 19, 2012

Related U.S. Application Data

(60) Provisional application No. 61/364,685, filed on Jul. 15, 2010.

(51) Int. Cl.
*A61N 1/36* (2006.01)
*A61N 1/05* (2006.01)

(52) U.S. Cl.
CPC ......... *A61N 1/3615* (2013.01); *A61N 1/3606* (2013.01); *A61N 1/36171* (2013.01); *A61N 1/0553* (2013.01)

(58) Field of Classification Search
CPC .............. A61N 1/3615; A61N 1/36171; A61N 1/3606; A61N 1/0553
USPC ..................................................... 607/2, 76
See application file for complete search history.

(56) References Cited

U.S. PATENT DOCUMENTS

| | | | |
|---|---|---|---|
| 6,516,227 B1 | 2/2003 | Meadows et al. | |
| 6,845,267 B2 * | 1/2005 | Harrison et al. | 607/3 |
| 6,895,280 B2 | 5/2005 | Meadows et al. | |
| 6,985,774 B2 * | 1/2006 | Kieval et al. | 607/44 |
| 6,993,384 B2 | 1/2006 | Bradley et al. | |
| 7,433,734 B2 * | 10/2008 | King | 607/2 |
| 7,539,538 B2 | 5/2009 | Parramon et al. | |
| 7,742,810 B2 | 6/2010 | Moffitt et al. | |
| 2003/0139781 A1 | 7/2003 | Bradley et al. | |
| 2005/0267546 A1 | 12/2005 | Parramon et al. | |
| 2007/0097593 A1 * | 5/2007 | Armstrong | 361/232 |
| 2008/0294226 A1 | 11/2008 | Moffitt et al. | |

OTHER PUBLICATIONS

Bhadra, Narendra et al., High frequency electrical conduction block of the pudendal nerve, J. Neural Eng. 3 (2006) 180-187.

(Continued)

*Primary Examiner* — Mark W Bockelman
(74) *Attorney, Agent, or Firm* — Schwegman Lundberg & Woessner, P.A.

(57) ABSTRACT

A neurostimulation system and method of blocking a neural axon. Time-varying electrical energy is conveyed to a blocking site on the neural axon for an initial phase. The conveyed electrical energy has an amplitude and frequency during the initial phase sufficient to block action potentials from propagating along the neural axon from a location proximal to the blocking site to a location distal to the blocking site. The time-varying electrical energy is conveyed to the blocking site on the neural axon for a subsequent phase contiguous with the initial phase. The conveyed electrical energy has a decreased amplitude and a frequency during the subsequent phase sufficient to maintain blocking of the action potentials along the neural axon from the location proximal to the blocking site to the location distal to the blocking site.

15 Claims, 8 Drawing Sheets

(56) References Cited

OTHER PUBLICATIONS

Bhadra, Niloy et al., Simulation of high-frequency sinusoidal electrical block of mammalian myelinated axons, J. Comput Neurosci (2007) 22:313-326.

Bhadra, Niloy et al, High-Frequency electrical conduction block of mammalian peripheral motor nerve, Muscle Nerve 32: 782-790, 2005.

Kilgore, K.L. et al., Nerve conduction block utilising high-frequency alternating current, Med. Biol. Eng. Comput., 2004, 42, 394-406.

* cited by examiner

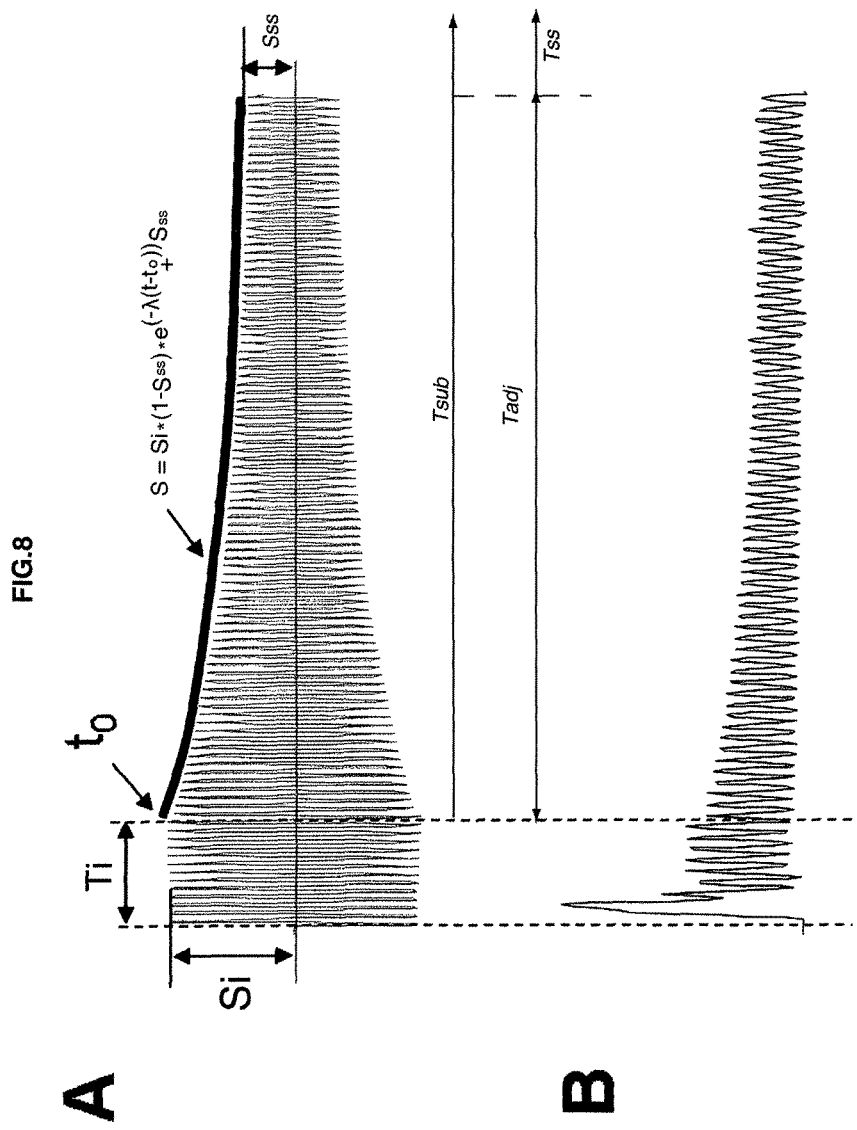

ENERGY EFFICIENT HIGH FREQUENCY NERVE BLOCKING TECHNIQUE

RELATED APPLICATION DATA

The present application claims the benefit under 35 U.S.C. §119 to U.S. provisional patent application Ser. No. 61/364,685, filed Jul. 15, 2010. The foregoing application is hereby incorporated by reference into the present application in its entirety.

FIELD OF THE INVENTION

The present inventions relate to tissue stimulation systems, and more particularly, to systems and methods for blocking the conduction of action potentials in nerves.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation electrode(s) to stimulate or activate a volume of tissue in accordance with a set of stimulation parameters and provide the desired efficacious therapy to the patient.

A typical stimulation parameter set may include the electrodes that are sourcing (anodes) or returning (cathodes) the stimulation current at any given time, as well as the amplitude, duration, and rate of the stimulation pulses. The neurostimulation system may further comprise a handheld patient programmer to remotely instruct the neurostimulator to generate electrical stimulation pulses in accordance with selected stimulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

To better understand the effect of stimulation pulses on nerve tissue, reference to FIG. 1 will now be made. As there shown, a typical neuron 1 that can be found in the white matter of the spinal cord or brain includes an axon 2 containing ionic fluid (and primarily potassium and sodium ions) 3, a myelin sheath 4, which is formed of a fatty tissue layer, coating the axon 2, and a series of regularly spaced gaps 5 (referred to as "Nodes of Ranvier"), which are typically about 1 micrometer in length and expose a membrane 6 of the axon 2 to extracellular ionic fluid 7.

When the neuron 1 is stimulated, e.g., via an electrical pulse, an action potential (i.e., a sharp electrochemical response) is induced within the neuron 1. As a result, a transmembrane voltage potential (i.e., a voltage potential that exists across the membrane 6 of the axon 3) changes, thereby conducting a neural impulse along the axon neuron 1 as sodium and potassium ions flow in and out of the axon 3 via the ion channels in the membrane 6. Because ion flow can only occur at the nodes 5 where the membrane 6 of the axon 3 is exposed to the extracellular ionic fluid 3, the neural impulse will actually jump along the axon 3 from one node 6 to the next node 6. In this manner, the myelin sheath 4 serves to speed the neural impulse by insulating the electrical current and making it possible for the impulse to jump from node 6 to node 6 along the axon 3, which is faster and more energetically favorable than continuous conduction along the axon 3. Further details discussing the electrochemical mechanisms involved with propagating an AP along a neuron are disclosed in U.S. patent Ser. No. 11/752,895, entitled "Short Duration Pre-Pulsing to Reduce Stimulation-Evoked Side-Effects," which is expressly incorporated herein by reference.

When stimulating target neural tissue, it is sometimes beneficial to block action potentials from being induced in neural tissue not targeted for stimulation in order to avoid adverse side-effects. For example, a high frequency sinusoidal signal can be applied at a location along the spinal cord to block action potentials evoked from a stimulation pulse from being propagated to a non-targeted site, as described in U.S. patent application Ser. No. 12/618,563, entitled "System and Method for Modulating Action Potential Propagation During Spinal Cord Stimulation," which is expressly incorporated herein by reference. The mechanism of high frequency nerve blocking is the depolarization of the transmembrane voltage potential at a node of Ranvier.

In particular, high frequency blocking is based on the inactivation of sodium channels created by high frequency oscillation of the axonal membrane. With reference to FIG. 2, a computational model shows that a high frequency sinusoidal generator can generate a high frequency sinusoidal signal (waveform A) that can be conveyed to a blocking site of a neuronal axon via a blocking electrode, resulting in a transmembrane voltage potential at the blocking site (waveform F) that oscillates with the applied high frequency sinusoidal signal. Typically, high frequency signals (i.e., signals greater than 2 KHz) evoke an initial action potential that propagates in both directions along the neural axon, as shown during an initial firing period in the transmembrane voltage potential at a node of Ranvier proximal to the blocking site (waveform E) and a transmembrane voltage potential at a node of Ranvier distal to the blocking site (waveform G). However, after the initial firing period, depolarization of the membrane at the blocking site (waveform F) is maintained as long as the high frequency blocking signal is applied. A stimulation pulse train (waveform D) applied to a stimulation site via a stimulation electrode B creates action potentials that propagate to the node of Ranvier proximal to the blocking site (waveform E), but that do not propagate to the node of Ranvier distal to the blocking site (waveform G).

One clinical problem associated with high frequency nerve blocking is that it requires a relatively high amount of power to implement in a clinical setting, since the threshold to block action potentials in a nerve is much higher than the threshold to evoke action potentials in the nerve. Thus, if the amplitude of the intended blocking electrical pulse is not high enough, it would instead stimulate the nerve fibers, potentially causing an adverse stimulation effect. Furthermore, the high frequency blocking signal must be maintained to maintain the blocking effect; otherwise, the nerve fibers will revert back to their normal condition, and will thus, propagate action potentials when stimulated.

Thus, a neurostimulation system and method that is capable of providing high frequency blocking signals in a more power efficient manner is needed.

SUMMARY OF THE INVENTION

In accordance with a first aspect of the present inventions, a neurostimulation system is provided. The system comprises at least one electrical terminal configured for being respectively coupled to at least one electrode locatable adjacent a blocking site of a neural axon, and analog output circuitry configured for conveying time-varying (e.g., sinusoidal) electrical energy to the at least one electrical terminal. The system further comprises control circuitry configured for instructing the analog output circuitry to convey the time-varying electrical energy during an initial phase and a subsequent phase. In one embodiment, the initial phase is in the range of 0.1-20 ms, and the subsequent phase is greater than the initial phase. An optional embodiment comprises a housing containing the electrical terminal(s), the analog output circuitry, and the control circuitry.

The conveyed electrical energy has an amplitude and frequency during the initial phase sufficient to block action potentials from propagating along a neural axon from a location proximal to the blocking site to a location distal to the blocking site. In one embodiment, the amplitude is uniform during the initial phase. Preferably, the frequency is greater than 2 KHz, and more preferably, in the range of 3 KHz-20 KHz.

The conveyed electrical energy has a decreased amplitude and optionally a decreased frequency during the subsequent phase sufficient to maintain blocking of the action potentials along the neural axon from the location proximal to the blocking site to the location distal to the blocking site. In one embodiment, the control circuitry is configured for automatically instructing the analog output circuitry to decrease the amplitude from an initial value at the end of the initial phase to a steady-state value during the subsequent phase. The subsequent phase may be divided into an amplitude adjustment phase and a steady-state phase, in which case, the control circuitry may be configured for instructing the analog output circuitry to gradually decrease the amplitude (e.g., exponentially or linearly) from the initial value to the steady-state value during the amplitude adjustment phase, and for instructing the analog output circuitry to maintain the amplitude at the steady-state value during the steady-state phase.

In an optional embodiment, the system further comprises at least another electrical terminal configured for being respectively coupled to at least another electrode locatable adjacent a stimulation site of the neural axon proximal to the blocking site. In this case, the analog output circuitry may be further configured for conveying stimulation pulses to the at least other electrical terminal, and the control circuitry may be further configured for instructing the analog output circuitry to convey the stimulation pulses during the initial phase and the subsequent phase to evoke the action potentials at the stimulation site.

In accordance with a second aspect of the present inventions, a method of blocking a neural axon is provided. The method comprises conveying time-varying (e.g., sinusoidal) electrical energy to a blocking site on the neural axon for an initial phase. The conveyed electrical energy has an amplitude and frequency during the initial phase sufficient to block action potentials from propagating along the neural axon from a location proximal to the blocking site to a location distal to the blocking site. In one method, the amplitude is uniform during the initial phase. Preferably, the frequency is greater than 2 KHz, and more preferably, in the range of 3 KHz-20 KHz.

The method further comprises conveying the time-varying electrical energy to the blocking site on the neural axon for a subsequent phase contiguous with the initial phase. The conveyed electrical energy has a decreased amplitude and optionally a decreased frequency during the subsequent phase sufficient to maintain blocking of the action potentials along the neural axon from the location proximal to the blocking site to the location distal to the blocking site. In one method, the initial phase is in the range of 0.1-20 ms, and the subsequent phase is greater than the initial phase. In one method, the amplitude is decreased from an initial value at the end of the initial phase to a steady-state value during the subsequent phase. The subsequent phase may be divided into an amplitude adjustment phase and a steady-state phase, in which case, the amplitude may be decreased (e.g., exponentially or linearly) from the initial value to the steady-state value during the amplitude adjustment phase, and the amplitude may be maintained at the steady-state value during the steady-state phase. An optional method further comprises applying stimulation pulses to a stimulation site during the initial phase and the subsequent phase to evoke the action potentials at the stimulation site, wherein the stimulation site is proximal to the blocking site.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a diagram illustrating the blocking effect of a neural axon using modulated high frequency energy applied by the SCS system of FIG. 3.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 3:
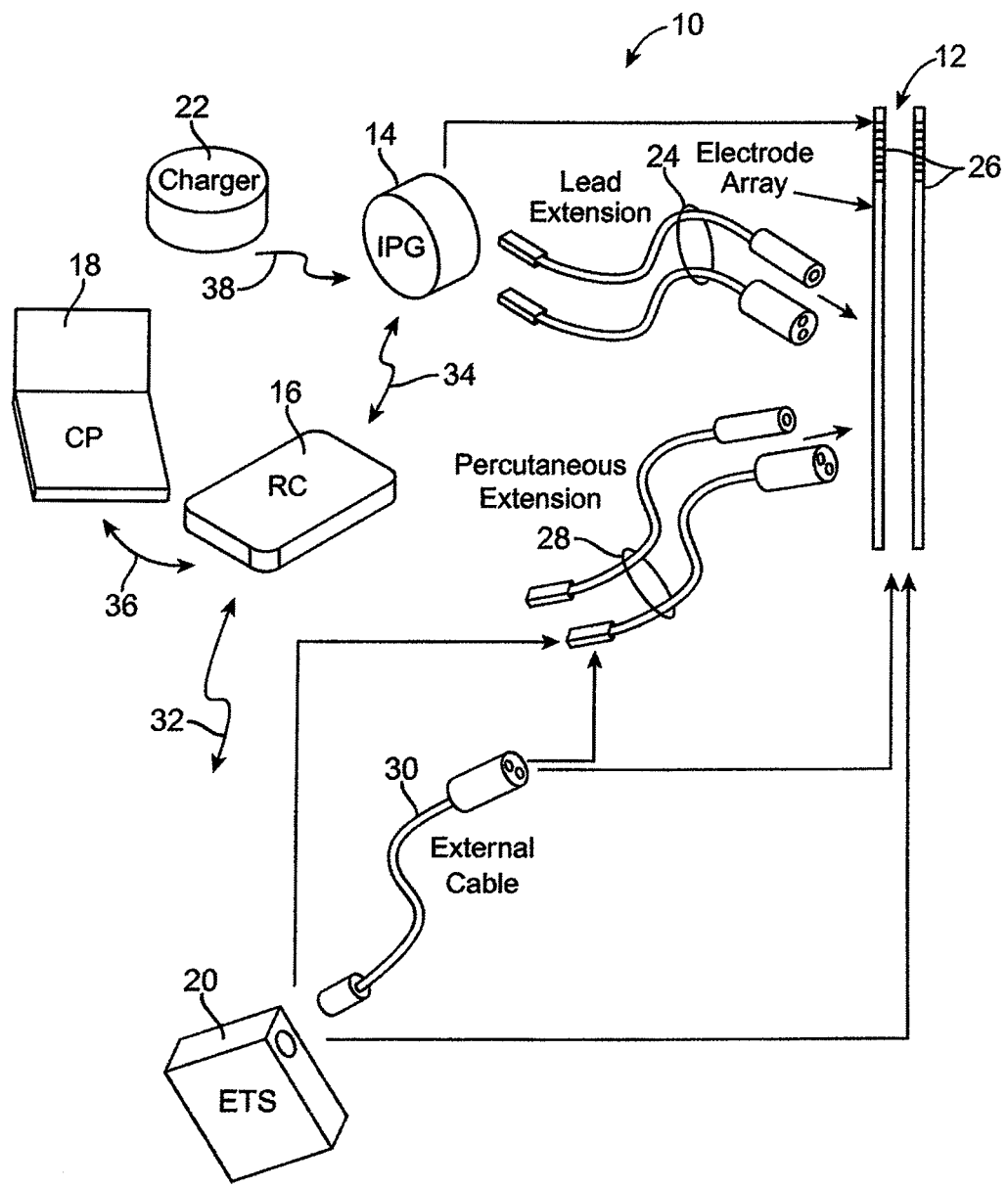
FIG. 3 is a plan view of one embodiment of a spinal cord stimulation (SCS) system arranged in accordance with the present inventions.

Turning first to FIG. 3, an exemplary spinal cord stimulation (SCS) system 10 generally includes one or more (in this case, two) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 4:
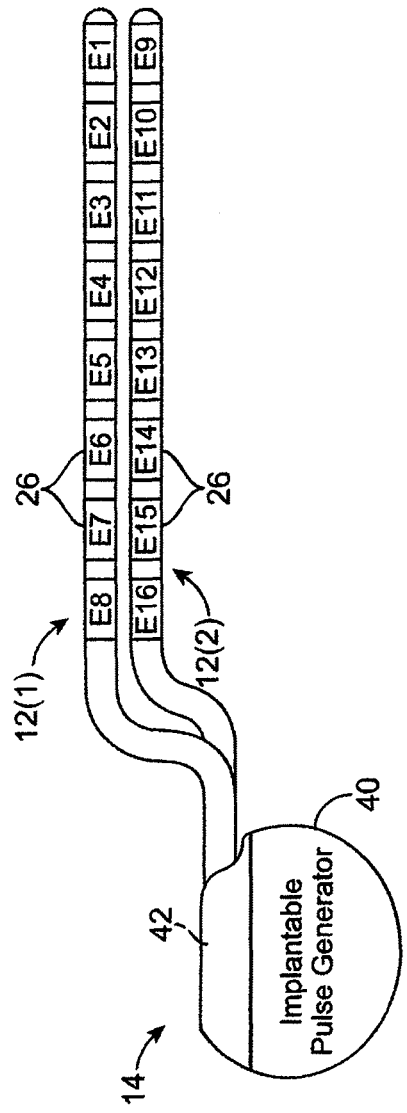
FIG. 4 is a plan view of an implantable pulse generator (IPG) and stimulation leads used in the SCS system of FIG. 3.

Referring now to FIG. 4, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case 40. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

The IPG 14 also comprises circuitry configured for delivering electrical energy to the electrode array 26 in a manner that blocks action potentials (APs) that propagate along neural axons (which in the illustrated embodiment, are the dorsal column (DC) neural fibers) in response to the pulsed electrical stimulation energy. In one embodiment, the electrical energy takes the form of a modulated high frequency signal capable of blocking the action potentials (APs) propagating along the DC neural fibers. Further details discussing the blocking electrical energy will be discussed below.

Figure 5:
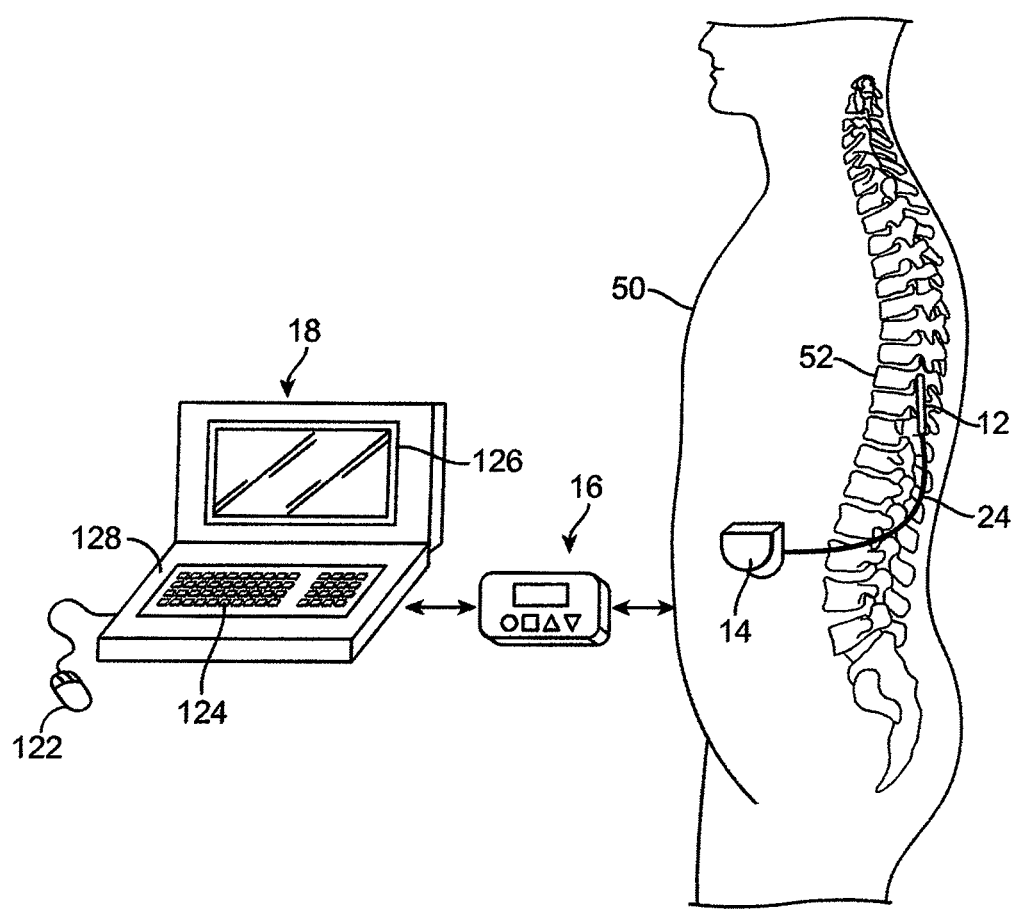
FIG. 5 is a plan view of the SCS system of FIG. 3 in use with a patient.

As shown in FIG. 5, the electrode leads 12 are implanted within the spinal column 52 of a patient 50. The preferred placement of the electrode leads 12 is adjacent, i.e., resting near, or upon the dura, adjacent to the spinal cord area to be stimulated. Due to the lack of space near the location where the electrode leads 12 exit the spinal column 52, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 6:
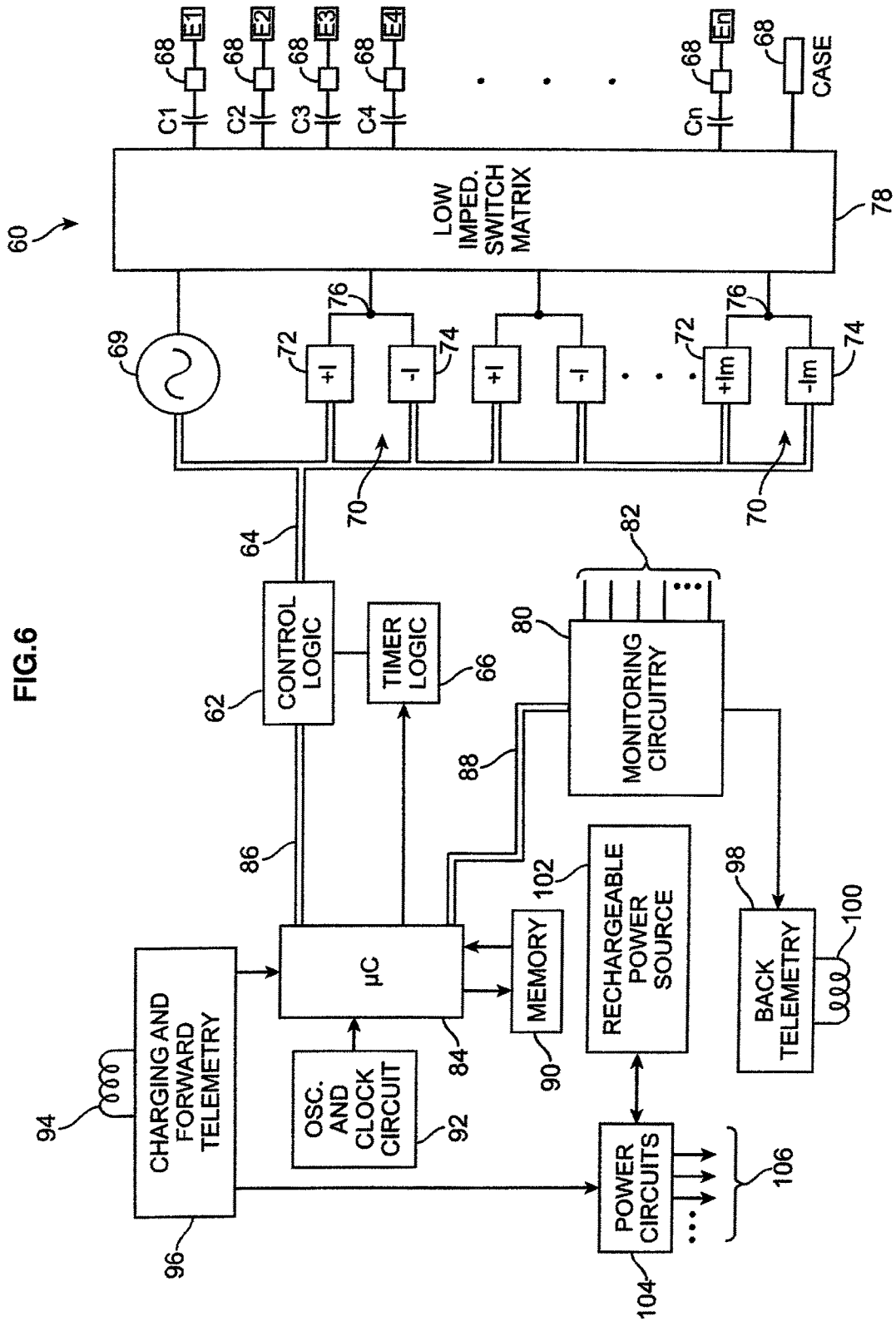
FIG. 6 is a block diagram of the internal components of the IPG of FIG. 4.

Turning next to FIG. 6, one exemplary embodiment of the IPG 14 will now be described. The IPG 14 includes analog output circuitry 60 configured for generating electrical stimulation energy in accordance with a defined pulsed waveform having a specified pulse amplitude, pulse rate, pulse duration, pulse shape, and burst rate under control of control logic circuitry 62 over data bus 64. The analog output circuitry 60 is further configured for generating AP blocking electrical energy, which in the illustrated embodiment, takes the form of a modulated high frequency sinusoidal signal.

Control of the pulse rate and pulse duration of the electrical stimulation waveform is facilitated by timer logic circuitry 66, which may have a suitable resolution, e.g., 10 µs. In the illustrated embodiment, the pulse rate can be varied within the range of 2 Hz-1200 Hz. The stimulation energy generated by the analog output circuitry 60 is output via capacitors C1-C16 to electrical terminals 68 corresponding to electrodes E1-E16.

The analog output circuitry 60 comprises a plurality m independent current source pairs 70 capable of supplying the stimulation energy to the electrical terminals 68 at a specified and known amperage. One current source 72 of each pair 70 functions as a positive (+) or anodic current source, while the other current source 74 of each pair 70 functions as a negative (−) or cathodic current source. The outputs of the anodic current source 72 and the cathodic current source 74 of each pair 70 are connected to a common node 76.

The analog output circuitry 60 comprises a sinusoidal source 69 capable of supplying the AP blocking electrical energy in the form of a sinusoidal signal to the electrical terminals 68 at a specified and known amperage. The frequency of the signal generating by the sinusoidal source 69 is preferably greater than the pulse rate of the stimulation energy. In the illustrated embodiment, the frequency of the sinusoidal signal is greater than 2 KHz, and preferably in the range of 3 KHz-20 KHz.

The analog output circuitry 60 further comprises a low impedance switching matrix 78 through which the common node 76 of each current source pair 70 is connected to any of the electrical terminals 68 via the capacitors C1-C16. Thus, for example, it is possible to program the first anodic current source 72 (+I1) to produce a pulse having a amplitude of +4 mA (at a specified rate and for a specified duration), and to synchronously program the second cathodic current source 74 (−I2) to similarly produce a pulse having a amplitude of −4 mA (at the same rate and pulse duration), and then connect the node 76 of the anodic current source 72 (+I1) to the electrical terminal 68 corresponding to electrode E3, and connect the node 76 of the cathodic current source 74 (−I2) to the electrical terminal 68 corresponding to electrode E1. The sinusoidal source 69 is also connected through the low impedance switching matrix 78 to any of the electrical terminals 68 via the capacitors C1-C16.

The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference. In an alternative embodiment, rather than using independent controlled current sources, independently controlled voltage sources for providing electrical pulses of a specified and known voltage at the electrical terminals 68 can be provided. The operation of this output circuitry, including alternative embodiments of suitable output circuitry for performing the same function of generating electrical pulses of a prescribed amplitude and width, is described more fully in U.S. Pat. Nos. 6,516,227 and 6,993,384, which are expressly incorporated herein by reference.

Hence, it is seen that each of the electrical terminals 68 can be programmed to have a blocking state (i.e., a sinusoidal current flows through the respective electrode), a stimulation state (i.e., a pulsed DC current (sourcing current or sinking current) flows through the respective electrode), or an off state (i.e., no current flows through the respective electrode). Further, the amplitude of the current for a given electrical terminal 68 may be programmed to one of several discrete levels.

In one embodiment, the current through each stimulating electrical terminal 68 can be individually set from 0 to ±10 mA in steps of 100 μA, within the output voltage/current requirements of the IPG 14. Additionally, in one embodiment, the total current output by a group of stimulating electrical terminals 68 can be up to ±20 mA (distributed among the electrodes included in the group). Moreover, it is seen that each of the stimulating electrical terminals 68 can operate in a multipolar mode, e.g., where two or more electrical terminals are grouped to source/sink current at the same time. Alternatively, each of the stimulating electrical terminals 68 can operate in a monopolar mode where, e.g., the electrical terminals 68 are configured as cathodes (negative), and case 40 of the IPG 14 is configured as an anode (positive). The peak-to-peak current of the sinusoidal signal conveyed through an AP modulating/blocking electrical terminal 68 can be individually set from 0 to ±10 mA in steps of 100 μA, within the output voltage/current requirements of the IPG 14. In the illustrated embodiment, the AP modulating/blocking electrical terminal 68 is operated in a monopolar mode where, e.g., the electrical terminal 68 is configured as an anode (positive) and the case of the IPG 14 is configured as a cathode (negative).

An electrical terminal 68 (whether stimulating or AP blocking) may be included with any of up to k possible groups, where k is an integer corresponding to the number of timing channels, and in one embodiment, is equal to 4, and with each timing channel k having a defined pulse amplitude, pulse duration, and pulse rate. Other timing channels may be realized in a similar manner. Thus, each channel identifies which electrical terminals 68 (and thus electrodes) are stimulating or AP modulating/blocking, as well as the characteristics of the current (pulse amplitude, pulse duration, pulse rate, and pulse shape for pulsed current, and peak-to-amplitude for sinusoidal current) flowing through the electrical terminals 68 (and thus electrodes).

The IPG 14 further comprises monitoring circuitry 80 for monitoring the status of various nodes or other points 82 throughout the IPG 14, e.g., power supply voltages, temperature, battery voltage, and the like. The monitoring circuitry 80 is also configured for measuring electrical data at the electrodes 26 (e.g., electrode impedance and/or electrode field potential) necessary to determine whether each of the electrodes 26 is functioning properly and is properly coupled to the IPG 14.

The IPG 14 further comprises processing circuitry in the form of a microcontroller (μC) 84 that controls the control logic circuitry 62 over data bus 86, and obtains status data, and optionally physiological information, from the monitoring circuitry 80 via data bus 88. The microcontroller 84 additionally controls the timer logic circuitry 66. The IPG 14 further comprises memory 90 and an oscillator and clock circuit 92 coupled to the microcontroller 84. Thus, the microcontroller 84, in combination with the memory 90 and oscillator and clock circuit 92, comprise a microprocessor system that carries out functions in accordance with a suitable program stored in the memory 90. Alternatively, for some applications, the functions provided by the microprocessor system may be carried out by a suitable state machine.

The microcontroller 84 generates the necessary control and status signals, which allow the microcontroller 84 to control the operation of the IPG 14 in accordance with the operating program and stimulation parameters stored in the memory 90. In controlling the operation of the IPG 14, the microcontroller 84 is able to individually generate stimulus pulses at the electrodes 26 using the analog output circuitry 60, in combination with the control logic circuitry 62 and timer logic circuitry 66, thereby allowing each electrode 26 to be paired or grouped with other electrodes 26, including the monopolar case electrode, and to control and modify the polarity, pulse amplitude, pulse rate, pulse duration, burst rate, and channel through which the current stimulus pulses are provided. The microcontroller 84 is also able to generate AP blocking electrical energy at selected ones of the electrodes 26 using the analog output circuitry 60, in combination with the control logical circuitry 62 and timer logic circuitry 66 (if needed), and to control and modify the pulse amplitude, pulse rate, pulse duration (if pulsed), and the channel through which the AP blocking electrical energy is provided.

The IPG 14 further comprises an alternating current (AC) receiving coil 94 for receiving programming data (e.g., the operating program and/or stimulation parameters) from the RC 16 in an appropriate modulated carrier signal, and charging and forward telemetry circuitry 96 for demodulating the carrier signal it receives through the AC receiving coil 94 to recover the programming data, which programming data is then stored within the memory 90, or within other memory elements (not shown) distributed throughout the IPG 14.

The IPG 14 further comprises back telemetry circuitry 98 and an alternating current (AC) transmission coil 100 for sending informational data sensed through the monitoring circuitry 80 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 102 and power circuits 104 for providing the operating power to the IPG 14. The rechargeable power source 102 may, e.g., comprise a lithium-ion or lithium-ion polymer battery. The rechargeable battery 102 provides an unregulated voltage to the power circuits 104. The power circuits 104, in turn, generate the various voltages 106, some of which are regulated and some of which are not, as needed by the various circuits located within the IPG 14. The rechargeable power source 102 is recharged using rectified AC power (or DC power converted from AC power through other means, e.g., efficient AC-to-DC converter circuits, also known as "inverter circuits") received by the AC receiving coil 104. To recharge the power source 102, an external charger (not shown), which generates the AC magnetic field, is placed against, or otherwise adjacent, to the patient's skin over the implanted IPG 14. The AC magnetic field emitted by the external charger induces AC currents in the AC receiving coil 104. The charging and forward telemetry circuitry 96 rectifies the AC current to produce DC current, which is used to charge the power source 102. While the AC receiving coil 104 is described as being used for both wirelessly receiving communications (e.g., programming and control data) and charging energy from the external device, it should be appreciated that the AC receiving coil 104 can be arranged as a dedicated charging coil, while another coil, such as coil 100, can be used for bi-directional telemetry.

It should be noted that the diagram of FIG. 6 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation lead 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Significant to the present inventions, it has been discovered that, given a particular frequency of blocking energy, the threshold for blocking action potentials along an axon is relatively high only for an initial time period, after which it drops for the same frequency as long as blocking of the axon is not interrupted after the initial time period. As such, the amplitude of the high frequency blocking energy need only be relatively high to initiate blocking of action potentials along the axon, after which it can be reduced to maintain blocking of the action potentials, thereby reducing the energy needed to effectively block an axon over the applicable period of time.

Figure 7:
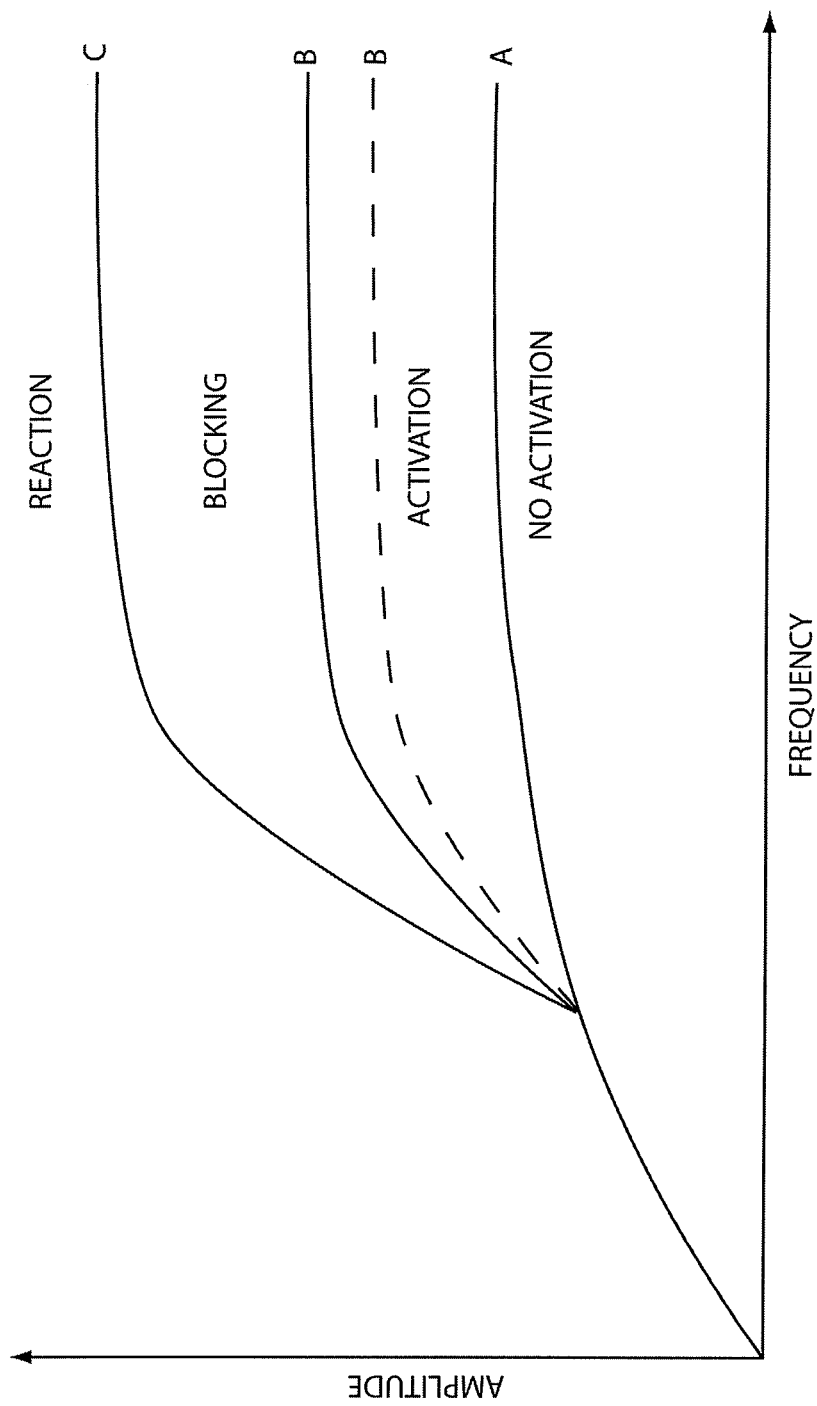
FIG. 7 is a diagram illustrating various amplitude thresholds of a neural axon as a function of frequency of an applied signal.

FIG. 7 is illustrative of this phenomenon. As there shown, various amplitude threshold curves are plotted as a function of the frequency of applied energy to a site on a neural axon. Curve A represents the amplitude threshold at which action potentials are evoked in the neural axon. Curve B represents the amplitude threshold at which action potentials are blocked in the neural axon. Curve C represents the amplitude threshold at which action potentials are reactivated in the neural axon. Thus, for purposes of blocking evoked potentials in the neural axon, it is desirable that the amplitude and frequency of the applied energy be such that the state of the neural axon is maintained between curves B and C. Significantly, curve B is represented by both a solid line that defines the amplitude threshold during an initial period, and a dashed line that defines the amplitude threshold during a subsequent period after blocking of the action potentials have been established. As can be seen, the dashed curve B is lower than the solid curve B, indicating that the amplitude of high frequency blocking energy can be reduced after the initial time period while maintaining the same blocking effect.

Figure 1:
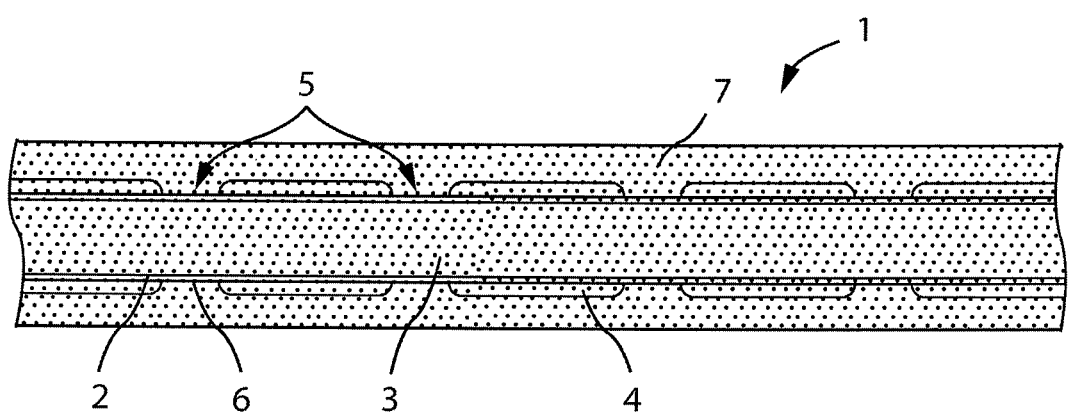
FIG. 1 is a plan view of a neural axon.
Figure 2:
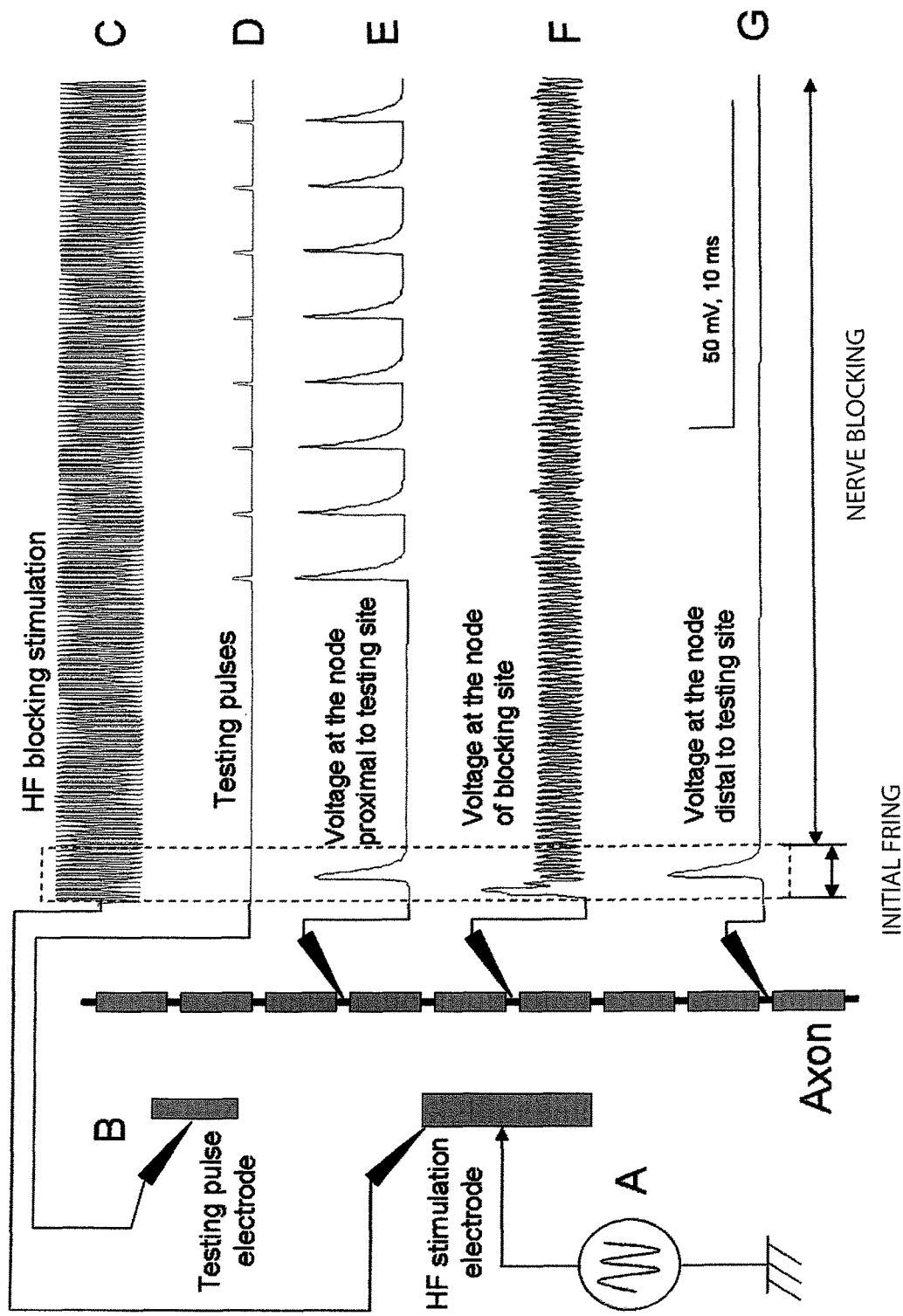
FIG. 2 is a diagram illustrating a prior art method of blocking action potentials from propagating along the neural axon of FIG. 1.

To this end, at least a first one of the electrodes 26 may be located adjacent to a stimulation site of a neural axon, at least a second one of the electrodes 26 may be located adjacent to a blocking site of a neural axon, the current sources 72/74 may be activated to convey electrical stimulation energy to first electrode(s) 26 via the corresponding electrical terminal(s) 68 to evoke action potentials that propagate distally along the neural axon from the stimulation site, and the sinusoidal source 69 may be activated to convey high frequency electrical blocking energy to the second electrode(s) 26 via the corresponding electrical terminal(s) 68 to block the action potentials from propagating along the neural axon distal to the blocking site in the same manner discussed above with respect to FIG. 2. However, instead of maintaining the blocking energy at a constant amplitude throughout the applicable time period, the control circuitry (in this case, the microcontroller 84 and associated control and timing logic 62/66) is configured for instructing the sinusoidal source 69 to modulate the blocking energy at different amplitudes.

In particular, the control circuitry instructs the sinusoidal source to convey the blocking energy during an initial phase and a subsequent phase. The initial phase is contiguous with the subsequent phase, such that the there is no interruption in the conveyance of the blocking energy. During the initial phase, the conveyed blocking energy has an amplitude and frequency sufficient to block action potentials from propagating along the neural axon from a location proximal to the blocking site to a location distal to the blocking site. During the subsequent phase, the conveyed blocking energy has a decreased amplitude and a frequency sufficient to maintain blocking of the action potentials along the neural axon from the location proximal to the blocking site to the location distal to the blocking site. Because the amplitude of blocking energy has been decreased, energy savings is achieved. Preferably, the duration of the initial phase is in the range of 0.1-20 ms to ensure that blocking of the action potentials has been established, while minimizing the time at which the amplitude of the high frequency blocking energy is relatively high to maximize energy savings. By the same token, the subsequent phase should be significantly greater than the initial phase in order to minimize the average amplitude of the high frequency blocking energy during the applicable time needed to block the action potentials.

For example, and with reference to FIG. 8, the control circuitry is configured for instructing the sinusoidal source 69 to automatically decrease the amplitude of the high frequency blocking energy from an initial value $S_i$ at the end of the initial phase $T_i$ to a steady-state value $S_{ss}$ during the subsequent phase $T_{sub}$, as shown by waveform A. As shown by waveform B, a computed transmembrane voltage of a model of the neural axon at the blocking site has an initial firing, but then is inactive for the last portion of the initial phase $T_i$ and throughout the entirety of the subsequent phase $T_{sub}$. As a result of the inactivation of the transmembrane voltage at the blocking site of the neural axon, action potentials will not propagate along the neural axon distal to the blocking site.

In the illustrated embodiment, the amplitude of the high frequency blocking energy during the initial phase $T_i$ is uniform to ensure that the neural axon is being effectively conditioned to block action potentials distal to the blocking site. However, the amplitude of the high frequency blocking energy may be decreased or increased during the initial phase $T_i$ as long as the transmembrane voltage at the blocking site of the neural axon is such that the blocking of the action potentials at the blocking site is firmly established.

As shown in FIG. 8, the subsequent phase $T_{sub}$ is divided into an amplitude adjustment phase $T_{adj}$ and a steady-state phase $T_{ss}$. Thus, the control circuitry is configured for instructing the sinusoidal source 69 to gradually decrease the amplitude from the initial value $S_i$ to the steady-state value $S_{ss}$ during the amplitude adjustment phase $T_{adj}$, and for instructing the sinusoidal source 69 to maintain the amplitude at the steady-state value $S_{ss}$ during the steady-state phase $T_{ss}$.

In the embodiment illustrated in FIG. 8, the control circuitry is configured for instructing the sinusoidal source 69 to exponentially decrease the amplitude of the high frequency blocking energy from the $S_i$ to the steady-state value $S_{ss}$ during the amplitude adjustment phase $T_{adj}$ in accordance with the equation $S=S_i*(1-S_{ss})*e^{(-\lambda*(t-t0))}+S_{ss}$, where $t_0$ is the time at the beginning of the amplitude adjustment phase $T_{adj}$, t is the instantaneous time, S is the amplitude of the high frequency blocking energy at any given time t, $S_i$ is the amplitude value of the high frequency blocking energy at time $t_0$, $S_{ss}$ is the peak steady-state amplitude value of the high frequency blocking energy during the steady-state phase $T_{ss}$, and $\lambda$ is the time constant that defines the exponential decline of the amplitude of the high frequency blocking energy. Although, the amplitude of the high frequency blocking energy has been specifically described as being exponentially decreased, the amplitude can be decreased in accordance with any function, such as being decreased in a linear fashion.

It should be noted that although the amplitude of the high frequency blocking energy is described as being decreased to a steady-state value $S_{ss}$, the amplitude of the high frequency blocking energy can be varied at any time during the subsequent phase $T_{sub}$ as long as blocking of the action potentials at the blocking site is contiguous during the applicable period of time. In effect, the subsequent phase $T_{sub}$ may not have a steady-state phase $T_{ss}$ at all. The significance is that the amplitude of the high frequency blocking energy during the subsequent phase $T_{sub}$ is, on average, less than the amplitude of the high frequency blocking energy during the initial phase $T_i$.

It should also be noted that the frequency of the high frequency blocking energy may be adjusted or set during either the initial phase $T_i$ or the subsequent phase $T_{sub}$ to minimize the amplitude of the high frequency blocking energy needed to maintain blocking of the action potentials. That is, it can be appreciated from FIG. 7 that, by decreasing the frequency of the blocking energy, the amplitude threshold of the blocking energy required to initiate or maintain the blocking effect decreases. Thus, the frequency of the blocking energy can be decreased within certain limits anytime during the initial phase, so that the amplitude of the high frequency stimulation energy can be initially reduced, or anytime during the subsequent phase, so that the amplitude of the high frequency stimulation energy can be reduced further than if the frequency had not been decreased, thereby further saving energy.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of blocking a neural axon, comprising:
conveying time-varying electrical energy to a blocking site on the neural axon for an
initial phase, wherein the conveyed electrical energy has an amplitude and frequency during the initial phase sufficient to block action potentials from propagating along the neural axon from a location proximal to the blocking site to a location distal to the blocking site; and
conveying the time-varying electrical energy to the blocking site on the neural axon for a subsequent phase contiguous with the initial phase, thereby treating pain suffered by a patient, wherein the conveyed electrical energy has, during the subsequent phase, a decreased amplitude relative to the initial phase and a frequency known to maintain blocking of the action potentials along the neural axon from the location proximal to the blocking site to the location distal to the blocking site, wherein the initial phase is in the range of 0.1-20 ms.

2. The method of claim 1, wherein the amplitude is uniform during the initial phase.

3. The method of claim 1, wherein the frequency of the conveyed electrical energy is greater than 2 KHz during the initial phase.

4. The method of claim 1, wherein the frequency of the conveyed electrical energy is in the range of 3 KHz-20 KHz during the initial phase.

5. The method of claim 1, wherein the time-varying electrical energy is sinusoidal.

6. The method of claim 1, wherein the subsequent phase is greater than the initial phase.

7. The method of claim 1, wherein the frequency of the conveyed electrical energy during the subsequent phase is a decreased frequency relative to the initial phase.

8. The method of claim 1, further comprising applying stimulation pulses to a stimulation site during the initial phase and the subsequent phase to evoke the action potentials at the stimulation site, wherein the stimulation site is proximal to the blocking site.

9. The method of claim 1, wherein the time-varying electrical energy is conveyed from at least one electrode implanted within a patient to the blocking site.

10. The method of claim 1, wherein the amplitude is automatically decreased from the initial value at the end of the initial phase to the steady-state value during the subsequent phase.

11. The method of claim 1, wherein the amplitude of the electrical energy conveyed during the subsequent phase varies, and is, on average, less than the amplitude of the electrical energy conveyed during the initial phase.

12. The method of claim 1, wherein the subsequent phase is greater than the initial phase.

13. The method of claim 1, wherein the neural axon is a spinal neural axon.

14. A method of blocking a neural axon, comprising:
conveying time-varying electrical energy to a blocking site on the neural axon for an initial phase, wherein the conveyed electrical energy has an amplitude and frequency during the initial phase sufficient to block action potentials from propagating along the neural axon from a location proximal to the blocking site to a location distal to the blocking site; and
conveying the time-varying electrical energy to the blocking site on the neural axon for a subsequent phase contiguous with the initial phase, thereby treating pain suffered by a patient, wherein the conveyed electrical energy has, during the subsequent phase, a decreased amplitude relative to the initial phase and a frequency known to maintain blocking of the action potentials along the neural axon from the location proximal to the blocking site to the location distal to the blocking site;
wherein the amplitude is decreased from an initial value at the end of the initial phase to a steady-state value during the subsequent phase, the subsequent phase is divided into an amplitude adjustment phase during which the amplitude is gradually decreased from the initial value to the steady-state value at the beginning of a steady-state phase during which the amplitude is maintained at the steady-state value, and the amplitude is exponentially decreased from the initial value to the steady-state value during the amplitude adjustment phase.

15. The method of claim 14, wherein the amplitude is exponentially decreased in accordance with the equation $S=S_i*(1-S_{ss})*e^{(-\lambda \cdot (t-t0))}+S_{ss}$ where $t_0$ is the time at the beginning of the amplitude adjustment phase, t is the instantaneous time, S is the amplitude of the time-varying electrical energy at any given time t, $S_i$ is the amplitude value of the time-varying electrical energy at time $t_0$, $S_{ss}$ is the peak steady-state amplitude value of the time-varying electrical energy during the steady-state phase, and A is the time constant that defines the exponential decline of the amplitude of the time-varying electrical energy.

* * * * *